United States Patent [19]

Brumwell

[11] Patent Number: 5,129,393
[45] Date of Patent: Jul. 14, 1992

[54] DUAL CHAMBER RATE RESPONSIVE PACEMAKER WITH VARIABLE REFRACTORY PERIOD

[75] Inventor: Dennis A. Brumwell, Bloomington, Minn.

[73] Assignee: Medtronic, Inc., Minneapolis, Minn.

[21] Appl. No.: 567,433

[22] Filed: Aug. 14, 1990

[51] Int. Cl.$^5$ ............................................. A61N 1/368
[52] U.S. Cl. ......................................... 128/419 PG
[58] Field of Search ............................... 128/419 PG

[56] References Cited

U.S. PATENT DOCUMENTS

| | | | |
|---|---|---|---|
| 3,648,707 | 3/1972 | Greatbatch | 128/419 P |
| 4,059,116 | 11/1977 | Adams | 128/419 PG |
| 4,344,437 | 8/1982 | Markowitz | 128/419 PG |
| 4,363,325 | 12/1982 | Koline et al. | 128/419 PG |
| 4,407,287 | 10/1983 | Herpers | 28/419 PG |
| 4,428,378 | 1/1984 | Anderson et al. | 128/419 PG |
| 4,467,807 | 8/1984 | Bornzin | 128/419 PG |
| 4,515,161 | 5/1985 | Wittkampf et al. | 128/419 PG |
| 4,539,991 | 9/1985 | Boute et al. | 128/419 PG |
| 4,554,921 | 11/1985 | Boute et al. | 128/419 PG |
| 4,712,556 | 12/1987 | Baker, Jr. | 128/419 PG |
| 4,890,617 | 1/1990 | Markowitz et al. | 128/419 PG |
| 4,920,965 | 5/1990 | Funke et al. | 128/419 PG |
| 4,998,974 | 3/1991 | Aker | 128/419 PG |

Primary Examiner—William E. Kamm
Assistant Examiner—Kennedy J. Schaetzle
Attorney, Agent, or Firm—Reed A. Duthler; Harold R. Patton

[57] ABSTRACT

An improved atrial synchronous, dual chamber pacemaker provided with a variable refractory period during which the pacemaker is not responsive to the sensed atrial contractions. The atrial refractory period is varied as a function of measured atrial and ventricular rates, and corresponds to a predetermined proportion of the lesser of the average interval separating the ventricular contractions and the average interval separating atrial contractions. The invention is particularly beneficial in the context of a VDD type pacemaker.

10 Claims, 6 Drawing Sheets

DUAL CHAMBER RATE RESPONSIVE PACEMAKER WITH VARIABLE REFRACTORY PERIOD

BACKGROUND OF THE INVENTION

This invention pertains generally to the field of electrical heart pacemakers and more specifically to pacemakers of the type in which pacing rate is regulated by means of a sensor responsive to the patient's need for cardiac output and to pacemakers adapted to operate in an atrial synchronous mode, generally referred to as "VDD" pacemakers.

VDD pacemakers are first disclosed in U.S. Pat. No, 3,648,707 issued to Wilson Greatbatch on Mar. 14, 1972. This pacemaker included electrodes for sensing contractions of the atrium and ventricle and a pulse generator for pacing the ventricle. After sensing a contraction of the ventricle or pacing the ventricle, a lower rate timer was restarted. If this timer expired, it triggered generation of a ventricular pacing pulse. Also included was an A-V interval timer, initiated in response to the sensing of an atrial contraction. On expiration of this timer, the ventricular pacing pulse would also be triggered. The pacemaker included a third timer, defining an upper rate interval initiated following ventricular pacing or sensing of a ventricular contraction. During the upper rate interval, time out of the A-V interval would not be effective to trigger a ventricular pacing pulse. This allowed for inhibition of the ventricular pulse generator in the event that a natural ventricular contraction followed a sensed atrial contraction. It also defined a maximum synchronous pacing rate, corresponding to the upper rate interval. If the atrial rate exceeded this rate, the pacing rate would fall to the higher of one-half of the sensed atrial rate or the rate determined by the lower rate timer.

An improvement to this pacemaker was set forth in U.S. Pat. No. 4,059,116 issued to Adams on Jan. 12, 1976, incorporated herein by reference in its entirety. In this pacemaker, rather than preventing generation of a ventricular stimulus in response to time out of the A-V interval during the upper rate interval, the stimulus was instead delayed until the expiration of the upper rate interval. In addition, a post-ventricular atrial refractory period was defined after each ventricular pacing pulse and each sensed ventricular contraction, during which an atrial contraction would not initiate timing of the A-V interval. The net result of these features was to produce a pacemaker which displayed an improved response to atrial contractions occurring at intervals less than the upper rate interval. The pacemaker in this case generated ventricular stimulation pulses separated by the upper rate interval, displaying gradually lengthening A-V intervals until an atrial contraction fell within the post-ventricular atrial refractory period. The pacemaker would resynchronize on the next subsequent atrial contraction, mimicking the natural condition known as Wenckebach behavior. In commercially marketed pacemakers employing the Adams invention, the behavior of the pacemaker in the presence of high natural atrial rates is referred to as "Pseudo-Wenckebach" upper rate behavior.

Recently, variation of pacing rate in response to sensed physiologic parameters, such as physical activity, oxygen saturation, blood pressure and respiration has been the subject of much research and development activity. U.S. Pat. No. 4,428,378 issued to Anderson et al discloses a pacemaker which varies its pacing rate in response to sensed physical activity. Pacemakers as described in this patent have been widely commercialized. A similar pacemaker, varying its pacing rate in response to variations in oxygen saturation, is disclosed in U.S. Pat. No. 4,467,807, issued to Bornzin.

Physiologic sensors have been integrated into dual chamber pacemakers, as illustrated in U.S. Pat. No. 4,890,617, issued to Markowitz et al on Jan. 2, 1990, incorporated herein by reference in its entirety. In this patent, a DDD type pacemaker having pacing intervals regulated by a sensor responsive to physical activity is disclosed. In this device, a fixed post-ventricular atrial refractory period is defined following each ventricular pacing pulse.

An additional dual chamber rate responsive pacemaker is disclosed in U.S. Pat. application Ser. No. 07/249,046 filed Sep. 23, 1988, by Barouh Berkovits for a "DUAL CHAMBER RATE RESPONSIVE PACEMAKER", also incorporated herein by reference in its entirety. In this pacemaker, atrial rate is monitored and, in response to an atrial rate in excess of a predetermined upper rate operation of the pacemaker is changed to desynchronize it from the atrium, with pacing rate controlled by a sensor of the patient's demand for cardiac output. This pacemaker also employed a fixed post-ventricular atrial refractory period.

An additional dual chamber, rate responsive pacemaker is described in the article entitled "Rate Responsive Dual Chamber Pacing", published in *Pace*, Vol. 9, Nov.-Dec. 1986, pp. 987–991. In this device, regulation of the pacing rate was determinable either by the natural atrial rate or the activity rate. The pacemaker was so configured that it would not follow atrial rates substantially in excess of the rate defined by the sensor. This was accomplished by extending the post-ventricular atrial refractory period in response to detection of an atrial rate substantially in excess of the sensor determined pacing rate.

Numerous patents have dealt with dual chamber pacemakers which vary their post-ventricular atrial refractory periods in an attempt to prevent generation of pacemaker mediated tachycardias (PMT's). One such pacemaker is disclosed in U.S. Pat. No. 4,920,965 issued May 1, 1990 for a "DUAL CHAMBER PACEMAKER WITH ADAPTIVE ATRIAL ESCAPE INTERVAL", incorporated herein by reference in its entirety. In this pacemaker, a post-ventricular atrial refractory interval is calculated based upon the time of occurrence of the atrial contraction, relative to the preceding ventricular pacing pulse or sensed ventricular contraction. This pacemaker gradually decreased its post-ventricular atrial refractory period in response to increasing natural atrial rates. Alternatively, it has been suggested to monitor the timing of atrial contractions with respect to previous ventricular contractions and if their timing indicates that the atrial contractions are probably retrograde P-waves, to extend the post-ventricular atrial refractory period beyond the measured time of occurrence of the retrograde P-waves. Such pacemakers are disclosed in U.S. Pat. Nos. 4,544,921 and 4,503,857, issued to Boute et al.

SUMMARY OF THE INVENTION

The present invention is embodied in a VDD pacemaker of the type generally described in the above-cited Greatbatch and Adams patents, which also employs a sensor of physiologic demand for cardiac output. In response to the sensor, the interval between succeeding ventricular pacing pulses in the absence of natural atrial activity is varied. Like the pacemakers described in the above-cited Aug. 13, 1990 Berkovits application and the Funke patent, in the event of atrial activity occurring at a rate greater than the rate determined by the sensor, the pacemaker will pace the ventricle at the atrial rate, up to a maximum tracking rate defined by the sum of the A-V interval and the post-ventricular atrial refractory period. In the present invention, the post-ventricular atrial refractory period is calculated in response to both the sensor determined ventricular pacing rate and the natural atrial rhythm. Unlike the pacemaker described in the above-cited Herpers article, the ventricular pacing rate will follow a high natural atrial rate, even in the presence of an indication by the sensor of low physical activity.

In the present invention, the post-ventricular atrial refractory period is calculated by determining the average interval separating natural atrial contractions (average A-A interval) and the average interval separating paced or sensed ventricular contractions (average V-V interval). An interval equal to a predetermined portion of the A-A interval (A-A ARP) and an interval corresponding to a predetermined portion of the average V-V interval (V-V ARP) are calculated. For example, these intervals may be 75% of the average A-A and V-V intervals, respectively. The V-V ARP and A-A ARP are compared, and the lesser of the two intervals is employed as a variable atrial refractory period (VARP).

At low activity levels and low atrial rates, an extended VARP will be provided, preventing the occurrence of premature atrial contractions from triggering generation of ventricular pacing pulses. The resulting extended post-ventricular refractory period (PVARP) also prevents retrograde conducted P-waves from triggering ventricular pacing and thereby initiating a pacemaker mediated tachycardia. Unlike the Herpers pacer, the pacemaker of the present invention retains the ability to track physiologically appropriate rapid natural atrial rates in the presence of low sensor indicated pacing rates by following a gradual increase in atrial pacing rate with a gradual decrease in the PVARP. Conversely, provision of a relatively short post-ventricular atrial refractory period in response to a high sensor based pacing rate but a low atrial rate still allows for synchronization with natural atrial contractions which occur at appropriately timed locations.

Further, in the situation most likely to trigger pacemaker mediated tachycardias, provision of a high, sensor based ventricular pacing rate in the presence of atrial bradycardia, the pacemaker can be programmed to assure that an average atrial rate based on retrograde P-waves will not be effective to maintain a pacemaker mediated tachycardia.

DETAILED DESCRIPTION OF THE PREFERRED EMBODIMENTS

Figure 1:
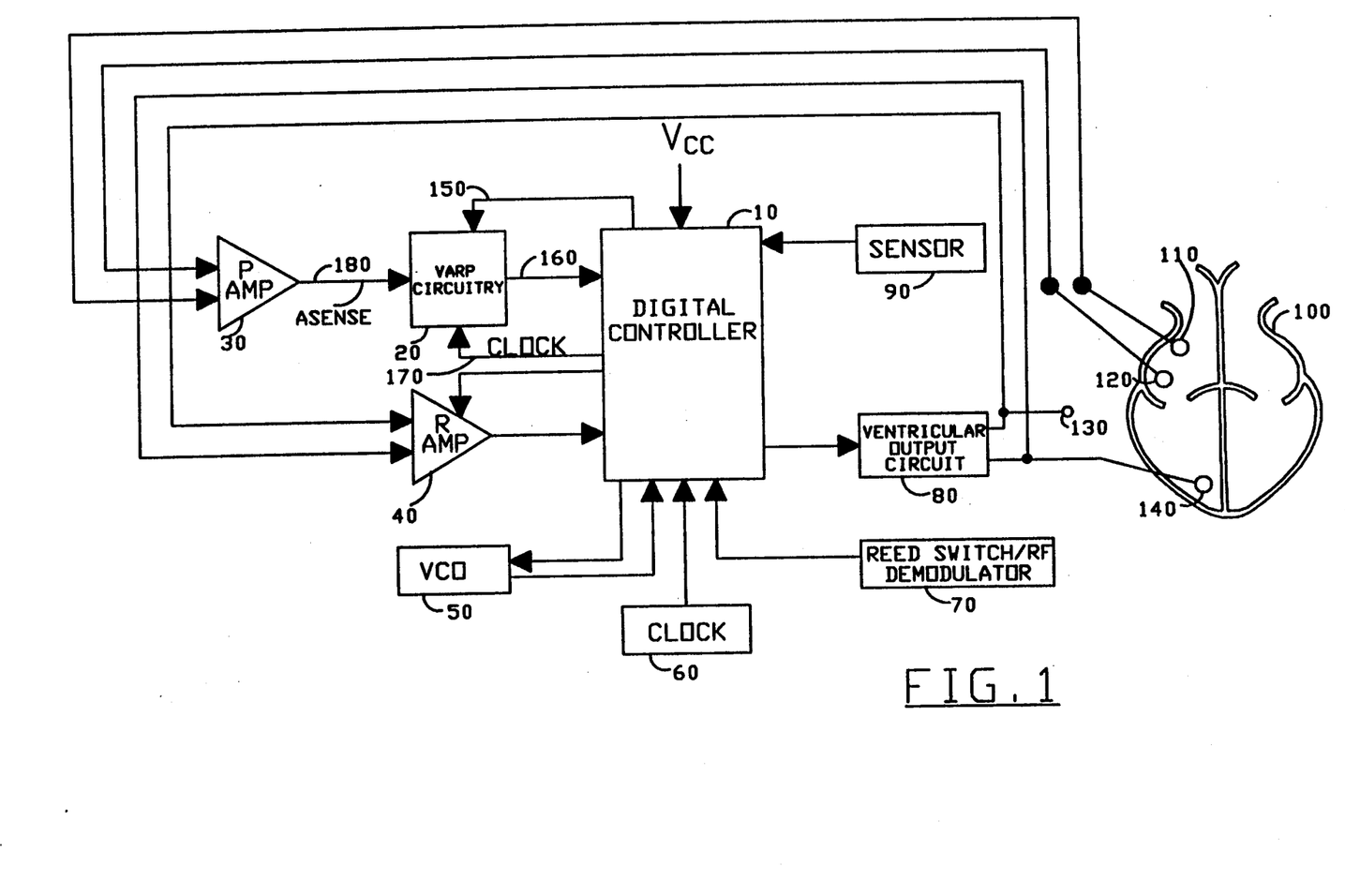
FIG. 1 is a block functional diagram of a pacemaker according to the present invention.

The present invention is believed employable in the context of any dual chamber, rate responsive pacemaker, but is particularly optimized for use in conjunction with a VVD type dual chamber pacemaker. FIG. 1 is intended to illustrate the general structural organization of an appropriate pacemaker for inclusion of the present invention. However, FIG. 1 should not be construed as limiting, as the invention is also believed employable in pacemakers of differing embodiments. For example, FIG. 1 discloses a pacemaker in which timing operations are controlled by digital circuitry. However, the invention might also be embodied in a pacemaker in which timing and control operations were accomplished using analog circuitry, as in the above-cited Adams and Greatbatch patents or in a pacemaker employing microprocessor control, as discussed in the above-cited Funke et al application.

Figure 2A:
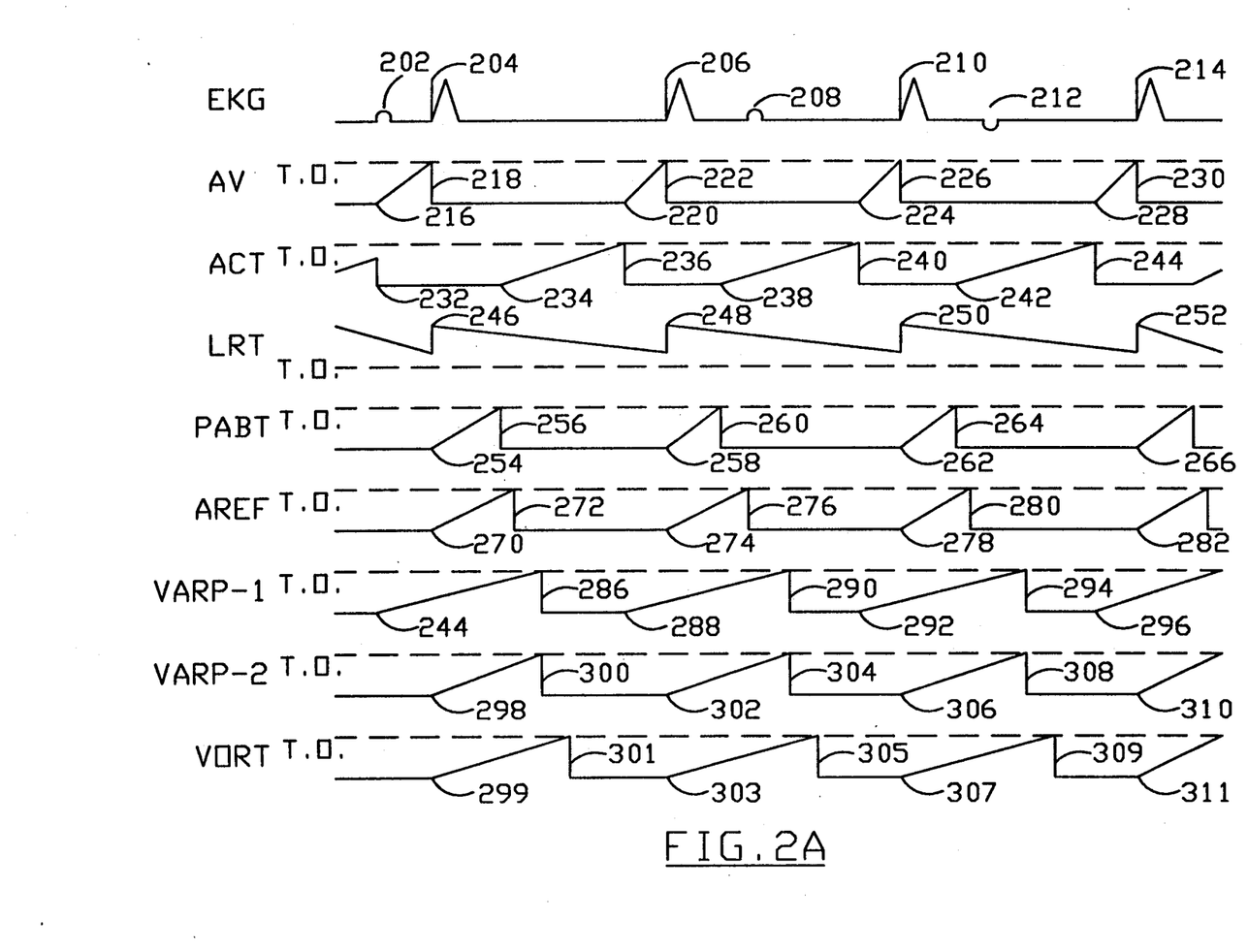
FIGS. 2A, 2B, and 2C illustrate the operation of the pacemaker illustrated in FIGS. 1, 3A and 3B.
Figure 2B:
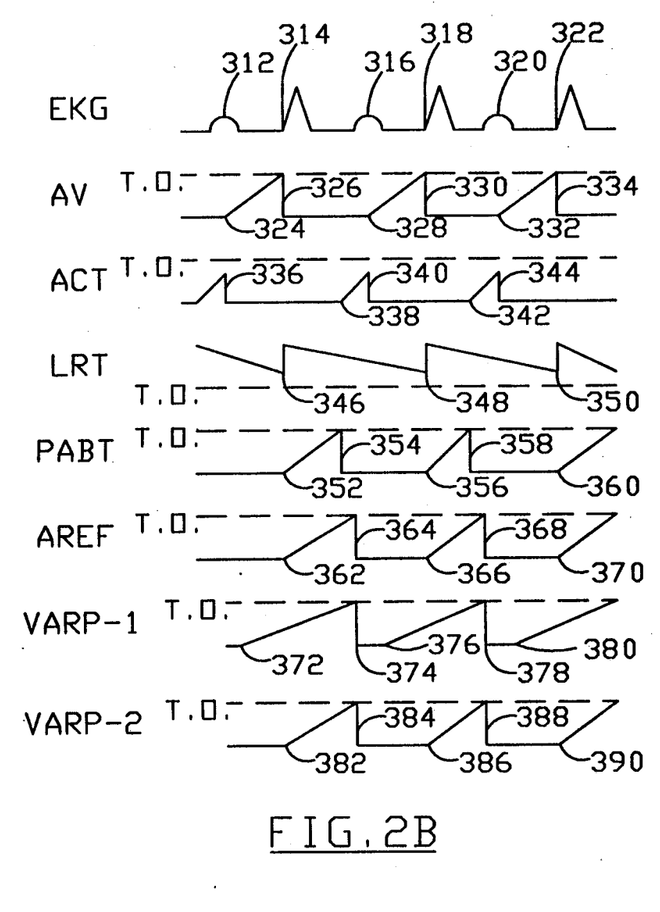
Figure 2C:
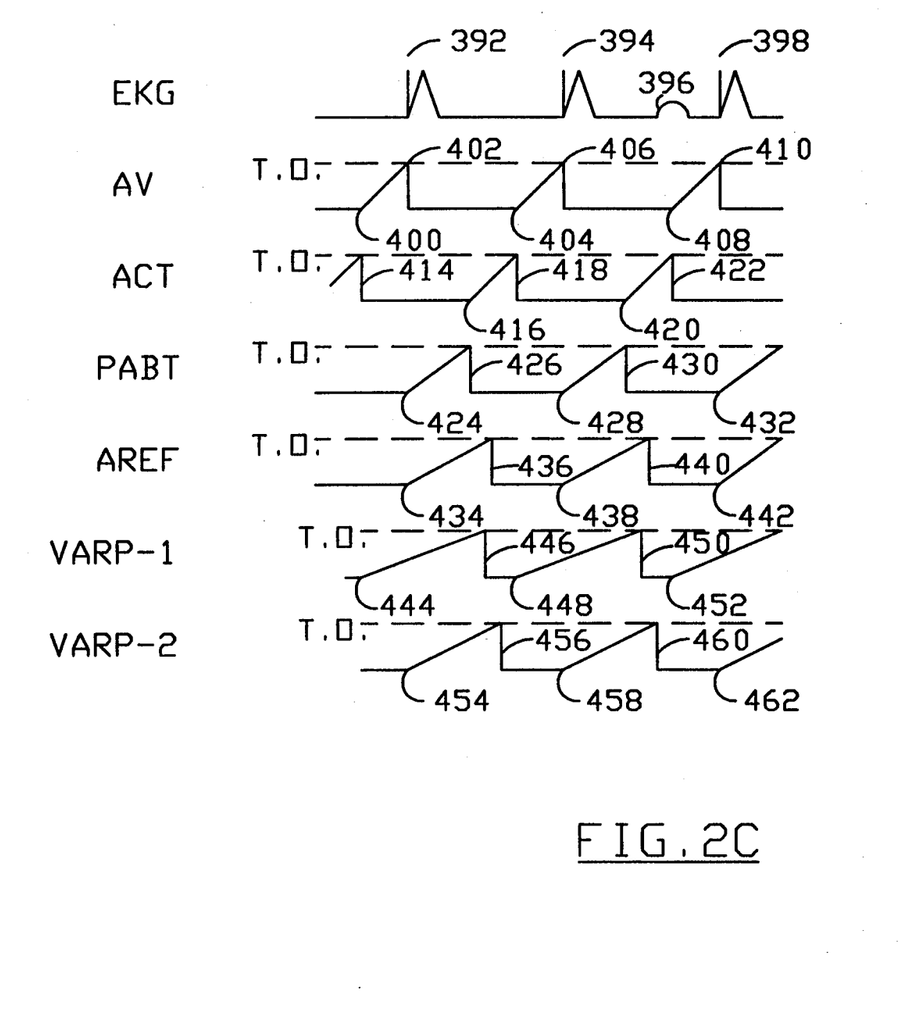

The basic functional operation of the pacemaker illustrated in FIG. 1 can be better understood in conjunction with the simulated EKG's and timing charts illustrated in FIGS. 2A-2C. With respect to these figures, it is assumed that the functioning of the digital controller corresponds to that of the pacemaker described in the above cited U.S. Pat. No. 4,890,617. Timing intervals and functions correspond to those illustrated in this patent, unless otherwise specified.

FIG. 1 is a block diagram illustrating the basic functional components of the pacemaker. The digital controller, as stated above, corresponds generally to the digital controller illustrated in U.S. Pat. No. 4,890,617, and provides all basic timing and control functions for the pacemaker. The pacemaker is coupled to the heart 100 by means of four electrodes 110, 120, 130 and 140. Electrodes 110 and 120 are both located on or in the atrium and serve to sense electrical signals indicative of atrial contractions. Electrode 130 is a subcutaneous electrode, typically taking the form of the can of the pacemaker. However it could alternately be placed on or in the ventricle of the heart. Electrode 140 is located on or in the ventricle of the heart. Electrodes 130 and 140 together serve to sense electrical signals indicative of contractions of the ventricles of the heart and to apply stimulating pulses to the heart to cause contractions of the ventricles of the heart. Electrodes 110, 120 and 140 may all be located on a single transvenous lead. Alternately, all four electrodes 110, 120, 130 and 140 might be located on a single transvenous lead or on separate atrial and ventricular leads.

Electrodes 110 and 120 are coupled to the inputs of atrial amplifier 30. Atrial amplifier 30 generates signals on ASENSE line 180 indicative of the occurrence of contractions of the atrium. Similarly, electrodes 130 and 140 are coupled to the inputs of ventricular amplifier 40, which provides signals indicative of ventricular contractions to the digital controller 10. Electrodes 130 and 140 are also Coupled to the outputs of ventricular output circuit 80, which applies stimulating pulses to the heart to cause contraction of the ventricles, under control of digital controller 10.

Sensor 90 may be any sensor of a physiologic parameter related to the demand for cardiac output. For example, it may be a sensor of physical activity, as disclosed in U.S. Pat. No. 4,428,378 issued to Anderson, et al, incorporated herein by reference in its entirety. Alternatively, sensor 90 may sense the oxygen saturation of the blood as disclosed in U.S. Pat. No. 4,807,629 issued to Baudino, et al, or right ventricular blood pressure as illustrated in U.S. Pat. No. 4,485,813 issued to Anderson, et al. Sensor 90 provides a digital controller 10 with a signal indicative of the physiologic demand for oxygenated blood. In turn, digital controller 10 employs this signal to vary the pacing rate of the pacemaker.

In its preferred embodiments, a pacemaker according to the present invention will be controllable by means of an RF link between an external programmer and the implanted pacemaker. Adjustment of the parameters of digital controller 10 is accomplished by means of reed switch/RF demodulator 70, which functions generally as disclosed in U.S. Pat. No. 4,401,120, issued to Hartlaub et al., also incorporated herein by reference in its entirety. Any programming/telemetry system according to the prior art may be used to perform this function. Crystal clock 60 provides timing signals to digital controller 10.

The output of atrial amplifier 30 passes through VARP circuitry 20, which functions as a variable refractory circuit, defining a variable refractory period. An atrial contraction sensed outside the refractory period defined by VARP circuitry 20 will be passed through on line 160 to digital controller 10. Following each such signal from atrial amplifier 30, VARP circuitry 20 defines a refractory period thereafter during which a subsequent signal on line 180 will not be allowed to pass through to digital controller 10. Clock line 170 provides a clock signal, allowing timing of this variable refractory period. VRATE line 150 provides input signals to VARP circuitry 20 indicative of the ventricular pacing rate determined by sensor 90. The rate of atrial contractions, indicated by signals on line 180 and the sensor regulated ventricular pacing rate, indicated by signals on VRATE line 150 together are used to calculate the duration of the variable refractory period determined by VARP circuitry 20.

As in the pacemaker described in the above-cited, Markowitz et al U.S. Pat. No. 4,890,617, the digital controller 10 defines a variable activity interval based on the output of sensor 90. On expiration of this interval, an atrial pacing pulse is triggered and the timer controlling the activity interval is reset. The timer controlling the activity interval is also reset in response to sensing of a natural atrial or ventricular contraction. Following either a atrial contraction or an atrial pacing pulse, an A-V interval is timed, at the expiration of which, in the absence of natural ventricular contractions, a ventricular pacing pulse is generated.

The digital controller 10 may provide a signal on line 150 each time the activity timer is reset. Because each resetting of the activity timer is followed by either generation of a ventricular pacing pulse or the sensing of a natural ventricular contraction, the rate at which such VRATE signals occur on line 150 is indicative of the activity-based ventricular pacing rate of the pacemaker and of the natural ventricular rate. Alternatively, digital controller 10 may provide a signal on line 150 with each sensed ventricular contraction and with each ventricular pacing pulse.

The rate at which atrial contractions are sensed by atrial amplifier 30 as reflected by signals on ASENSE line 180 indicates the natural atrial rate. VARP circuitry 20 averages the intervals between signals on line 180 and the intervals between signals on line 150. These averages are compared, and a portion of the lesser of the two averages is used as a variable refractory period initiated on each occurrence of a signal on line 180, provided that this refractory period is not presently in effect. Alternatively, if the signals on line 150 correspond to ventricular pacing or sensing, the variable refractory period may be initiated with each occurrence of a signal on line 150.

Digital Controller 10 performs various timing functions, which are illustrated as individual timers. However, for purposes of the present invention, it is not required that separate timers be used for each timing function. Functionally, controller 10 includes timers which define an A-V interval (AVT), an activity interval (ACT), a lower rate interval (LRT), an atrial blanking interval (PABT), a ventricular upper rate interval (VURT) and a fixed atrial refractory interval (AREF).

The operation of the pacemaker can be understood by following the simulated EKG strip uppermost in FIG. 2A, in conjunction with the timing diagrams below. A natural atrial contraction 202 passes through PVARP circuitry 20 and initiates timing of a 150 ms AV interval by digital controller 10 at 216. The occurrence of the atrial contraction also resets the activity timer at 232. On the time-out of the AV interval at 218, digital controller 10 triggers the ventricular output circuit 80 to generate a ventricular pacing pulse 204 which causes a ventricular contraction. At this time, the lower rate timer is reset and restarted at 246. This timer determines the base ventricular pacing rate of the pacemaker and is restarted after each sensed ventricular contraction and after each ventricular pacing pulse. On time-out of the lower rate interval, a ventricular pacing pulse will be triggered. The AV timer is generally initiated in response to sensing a natural atrial contraction or in response to time-out of the activity interval. The lower-rate timer therefore only controls the ventricular pacing rate in circumstances in which the atrial rate is slower than the pacing rate determined by the lower-rate timer and there is no significant physical activity.

Also concurrent with generation of the ventricular pacing pulse at 204, a 200 ms atrial blanking interval (PABT) is initiated at 254, a 250 ms fixed atrial refractory interval (AREF) is initiated at 270 and an upper rate interval (VURT) is initiated at 299. During the atrial blanking interval, signals on line 160 indicative of atrial contractions are not sensed by the digital controller 10. During the atrial refractory interval, signals on line 160 indicative of atrial contractions are ineffective to initiate timing of A-V intervals. Time-out of the AV interval during the upper rate interval will cause triggering of a ventricular pacing pulse at the time-out of the upper rate interval.

On time-out of the atrial blanking interval at 256, the activity interval is initiated at 234. Shortly thereafter, the fixed atrial refractory interval times out at 272. On time-out of the activity interval at 236, the A-V interval is initiated at 220, with a pacing pulse 206 triggered on time-out of the A-V interval at 222. This much of the operation of the device corresponds to the pacemaker disclosed in the above-cited Markowitz patent, with the exception that in the Markowitz device, an atrial pacing pulse would normally be generated on time-out of the activity interval at 236. This difference in operation has important consequences with regard to the invention of the present patent application.

The timing diagrams illustrated in FIG. 2A, labeled VARP-1 and VARP-2 represent alternative operational embodiments of the VARP circuitry 20. The timing chart labeled VARP-1 corresponds to the operation of the circuitry specifically disclosed in FIGS. 3A and 3B. This circuitry defines a variable refractory period which is initiated with each resetting of the activity timer, as indicated by corresponding signals on line 150. The timing diagram labeled VARP-2 illustrates an alternative embodiment in which the variable refractory period is initiated concurrently with each ventricular contraction or each ventricular pacing pulse, as indicated by corresponding signals on line 150. The circuitry of FIGS. 3A and 3B would have to be slightly modified to provide this function, as discussed below. The variable refractory period VARP-2 would be equal to a lesser portion of the measured average A-A and V-V intervals. For example, a variable atrial refractory period initiated with each resetting of the activity timer would typically be in the range of 75% of the lesser of the averaged A-A and V-V intervals. A variable refractory period initiated with each ventricular pacing pulse or ventricular contraction would typically be equal to about 60% of the lesser of the averaged A-A and V-V intervals. In the timing diagrams illustrated in FIGS. 2A through 2D, these percentages are used to define the variable refractory intervals illustrated.

The VARP circuitry 20 addresses two problems which sometimes arose in the context of prior art VDD pacemakers. Because VDD pacemakers do not pace in the atrium, a ventricular pacing pulse at the expiration of the lower rate interval may not be preceded by an atrial contraction. As such, if the natural atrial rate is lower than the rate defined by the lower rate timer, atrial contractions may occur closely following a paced ventricular contraction. Assuming that the atrial contraction does not fall within a refractory period, it will initiate time with the A-V interval and thereby cause generation of a ventricular pacing pulse at the earliest of the time-out of the A-V interval or the upper rate interval. The result will be two ventricular pacing pulses spaced inappropriately close to one another, given the activity level of the patient. If the second ventricular pacing pulse occurs at the end of the upper rate interval, it may be sufficiently remote in time from the preceding sensed atrial contraction to allow for retrograde conduction from the ventricle to the atrium. In this case, if the retrograde-conducted contraction occurs outside of the pacemaker's atrial refractory period, it will trigger timing of the A-V delay and generation of a subsequent pacing pulse at the time-out of the upper rate interval. This behavior, when it persists, is known as pacemaker mediated tachycardia. This behavior might also be initiated as a result of a ventricular pacing pulse at the expiration of the lower rate interval, not preceded by an atrial contraction.

The variable refractory periods provided in the pacemaker of the present invention address both of these problems by providing an extended post-ventricular refractory period in conditions of low atrial rate and low sensor-indicated pacing rate. The extended refractory period prevents closely coupled ventricular pacing pulses as a result of atrial bradycardia and prevents initiation of pacemaker-mediated tachycardia due to retrograde conduction, under these circumstances. The pacemaker, however, can still track naturally occurring high atrial rates, even in the presence of low sensor-indicated pacing rates. This is illustrated in FIGS. 2A and 2B.

In FIG. 2A, it is assumed that the patient is experiencing an atrial rate substantially slower than the activity indicated pacing rate. For purposes of FIG. 2A, the activity indicated pacing rate is equal to about 70 beats per minute, with average V-V intervals therefore equal to about 850 milliseconds. As a result, with each resetting of the activity timer at 232, 236, 240 and 244, the VARP-1 interval is initiated at 244, 288, 292 and 296, respectively. These refractory periods expire approximately 635 milliseconds later, at 286, 290 and 294. Similarly, the alternative VARP-2 periods initiated at 298, 302, 306 and 310 extend for approximately 60% of the average V-V interval, and expire approximately 510 milliseconds after initiation, at 300, 304 and 308.

Operation of the variable refractory period circuitry under the assumptions set forth with regard to FIG. 2A is as follows. Following a ventricular pacing pulse at 206, the lower rate timer is reset at 248, with the atrial blanking and atrial refractory time intervals initiated at 258 and 274, respectively. At time-out of the blanking interval at 260, the activity interval is initiated at 238. After the expiration of the fixed atrial refractory period at 276, a natural atrial contraction 208 occurs. However, because contraction 208 falls within both of the variable refractory periods VARP-1 and VARP-2, it is not sensed and is ineffective to initiate timing of an A-V interval. As such, time out of the activity timer at 240 initiates timing of the A-V interval at 224. Time-out of the A-V interval at 226 triggers a generation of a ventricular pacing pulse at 210, resetting of the lower rate timer at 250, and initiation of the atrial blanking and atrial refractory intervals at 262 and 278.

On expiration of the atrial blanking interval at 264, the activity interval is initiated at 242. Following time-out of the atrial refractory interval at 280, a retrograde P-wave 212 occurs. Occasionally, stimulation of the ventricle as at 210, separated in time from a preceding atrial contraction by a sufficient time interval may cause reverse conduction from the ventricle to the atrium, initiating contraction of the atrium and generating the electrical signal at 212 typically referred to as a "retrograde P-wave." Because the timing of this atrial contraction is not related to physiologic demand for cardiac output, it should be ignored by the pacemaker. Because it occurs during the variable refractory periods, it is in fact ignored by the pacemaker, and does not restart the timing of the A-V interval. Pacemaker mediated tachycardia is avoided. Instead, as previously discussed, time-out of the activity interval at 244 initiates timing of the A-V interval at 228, causing generation of a ventricular pacing pulse 214 on time-out of the A-V interval. If retrograde conduction persists, the atrial contractions will occur at the same rate as the ventricular pacing pulses and thus will not alter the variable refractory intervals.

As such, the variable refractory period provided by VARP circuitry 20 provides protection against tracking of bradycardic atrial contractions closely spaced to previous ventricular pacing pulses, and also prevents tracking of retrograde P-waves. The pacemaker instead provides ventricular pacing pulses separated by a V-V interval corresponding to the activity determined pacing rate.

The variable refractory periods provided by VARP circuitry 20 do not prevent the pacemaker from responding to natural, high atrial rates in the presence of a low sensor-indicated pacing rate. Because the atrial contractions are averaged by the VARP circuitry regardless whether they are used to initiate timing of an A-V interval, an increase in the natural atrial rate will cause a decrease in the calculated average A-A interval, and a corresponding decrease in the variable refractory intervals. While the pacemaker will not respond immediately to an abrupt increase in the natural atrial rate, upon updating of the average A-A interval, the variable refractory period will be reduced to less than the sensed atrial rate, allowing the pacemaker to thereafter follow the naturally high atrial rate. This is illustrated in FIG. 2B.

The simulated EKG in FIG. 2B assumes that the patient is exhibiting a high natural atrial rate. For purposes of FIG. 2B, it is assumed that the patient's natural atrial rate is substantially higher than the sensor determined pacing rate. As illustrated, natural atrial contractions 312, 316 and 320 are occurring at intervals of approximately 450 milliseconds or at a rate of about 130 beats per minute. As a result, the variable refractory periods VARP-1 initiated at 372, 376 and 380 extend for approximately 337 milliseconds after each atrial contraction, expiring at 374 and 378 as illustrated. In the presence of high natural atrial rates, it is assumed that atrial contractions closely spaced to previous ventricular pacing pulses are indicative of the body's demand for cardiac output, and therefore are desirably used to cause generation of ventricular pacing pulses. As illustrated, P-waves 312, 316 and 320 occur outside of VARP-1 and thus are effective to initiate timing of the A-V interval at 324, 328 and 332, with time-out of the A-V interval at 326, 330 and 334 triggering generation of ventricular pacing pulses 314, 318 and 322. Similarly, the alternate variable refractory VARP-2, calculated as 60% of the lesser of the averaged A-A and V-V interval, is initiated with each ventricular pacing pulse, at 382, 386 and 390, and extends for 270 milliseconds thereafter.

It is also important to note that the activity timer is reset at 336, 340 and 344 so that the average V-V interval calculated by VARP circuitry 20 will also be 450 milliseconds, the same as the average A-A interval. However, should the atrial rate decrease, the ventricular pacing rate will also correspondingly decrease, allowing both the average A-A and V-V intervals to decrease together, down to the point where the activity determined pacing rate is greater than the natural atrial rate, at which point the average A-A and V-V intervals will diverge.

In this illustration it can be seen that the fixed atrial refractory period determined by the digital controller 10 may determine the absolute maximum upper tracking rate of the device. Again, assuming that the A-V interval is equal to 150 milliseconds and the fixed atrial refractory period is equal to 250 milliseconds, this assures that the pacemaker will not track atrial contractions at a rate exceeding 150 beats per minute (separated by intervals of less than 400 milliseconds). This is important, as in situations in which the atrial rate is abnormal, such as in cases of atrial flutter, the average A-A interval would be quite short, resulting in an extremely short variable refractory period. The fixed atrial refractory period defined by the digital controller 10 serves a useful function in such circumstances.

The remainder of the operation of the device corresponds to the operation illustrated in FIG. 2A, with the atrial blanking interval initiated with each ventricular pacing pulse at 352, 356 and 360 and the fixed atrial refractory interval initiated at 362, 366 and 370. Expiration of the atrial blanking interval at 354 and 358 initiates timing of the activity interval at 338 and 342. Expiration of the fixed atrial refractory interval at 364 and 368 in this case occurs prior to expiration of the VARP-2 variable refractory intervals at 384 and 388. However, the VARP-1 intervals time-out at 374, 378 prior to time-out the fixed AREF refractory intervals. In this case, the fixed (AREF) atrial refractory interval would dictate the maximum atrial tracking rate as discussed above.

FIG. 2C illustrates the operation of the pacemaker of the present invention in circumstances in which the sensor determines a relatively rapid pacing rate, in this case approximately 120 beats per minute (500 ms average V-V intervals), while the natural atrial rate is substantially lower. In this case, the sensor-based ventricular pacing rate determines the effective variable refractory periods. In these circumstances, some benefit of atrial synchronization is still available as a result of the relatively short postventricular atrial refractory periods.

Operation of the pacemaker as illustrated begins with time-out of the activity interval at 414, initiating timing of the A-V interval at 400 and timing of VARP-1 at 444. On time-out of the A-V interval at 402, a ventricular pacing pulse is generated at 392. Simultaneously, the atrial blanking interval is initiated at 424, the fixed atrial refractory interval is initiated at 434 and the VARP-2 is initiated at 454. On time-out of the atrial blanking interval at 426, the activity interval is initiated at 416. On time-out of the activity interval at 418, the A-V interval is initiated at 404. On time-out of the A-V interval at 406, a ventricular pacing pulse is issued at 394, again causing initiation of the atrial blanking interval at 428, the fixed atrial refractory interval at 438 and VARP-2 at 458. On time-out of the atrial blanking interval at 430, the activity interval is initiated at 420. However, atrial contraction 396 occurs prior to time-out of the activity interval, causing reset of the activity interval timer at 422 and initiation of the A-V interval at 408. Because atrial contraction 396 occurs after time-out of the fixed atrial refractory period at 440, the time-out of the VARP-1 at 450 and VARP-2 at 460, atrial contraction 396 is effective to initiate timing of the A-V interval.

With an average ventricular interval of 500 ms, the duration of VARP-1 is approximately 375 ms from each resetting of the activity timer, providing a postventricular refractory period of approximately 225 ms. As such, in this case, it times out prior to the expiration of the fixed atrial refractory interval. VARP-2 extends for 300 ms following a ventricular contraction, and thus times out slightly after the fixed atrial refractory interval. This illustrates an important difference between the alternative approaches to calculating the variable atrial refractory period. Because VARP-1, initiated on reset of the activity timer always includes the A-V interval, the effective postventricular atrial refractory period provided by VARP-1 decreases proportionately more quickly than the effective postventricular atrial refractory period provided by VARP-2, initiated on ventricular pacing pulses or ventricular contractions.

In patients who may have relatively long retrograde conduction times, it may thus be advantageous to employ the functional embodiment illustrated as VARP-2. Alternatively, if a variable refractory period initiated on activity timer reset is employed, it may be advantageous in such patients to shorten the A-V interval to correspondingly lengthen the portion of VARP-1 extending beyond ventricular pacing pulses. Modification of the percentage of the average A-A or V-V interval calculated by VARP circuitry 20 is also an alternative programming option in such cases.

Figure 3A:
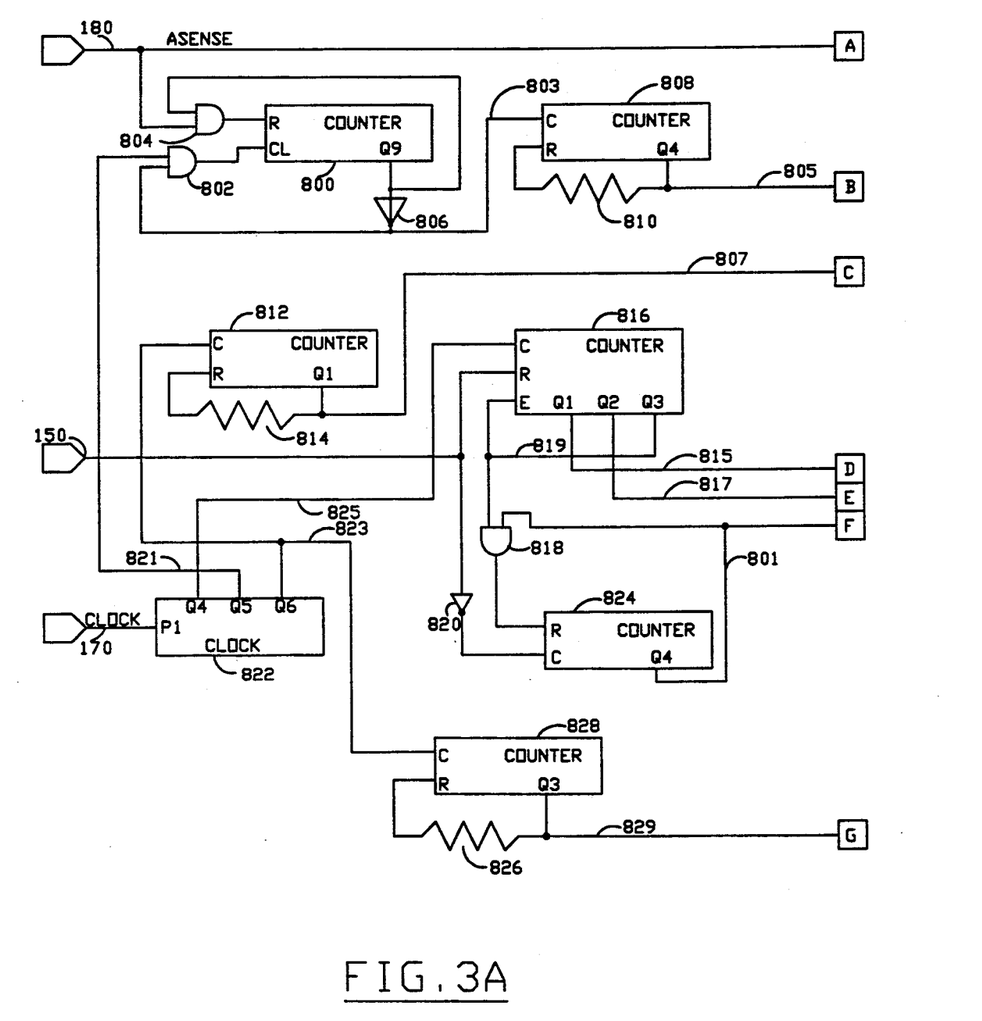
FIGS. 3A and 3B are schematic diagrams of the circuitry for controlling the post-ventricular atrial refractory period in the pacemaker illustrated in FIG. 1.
Figure 3B:
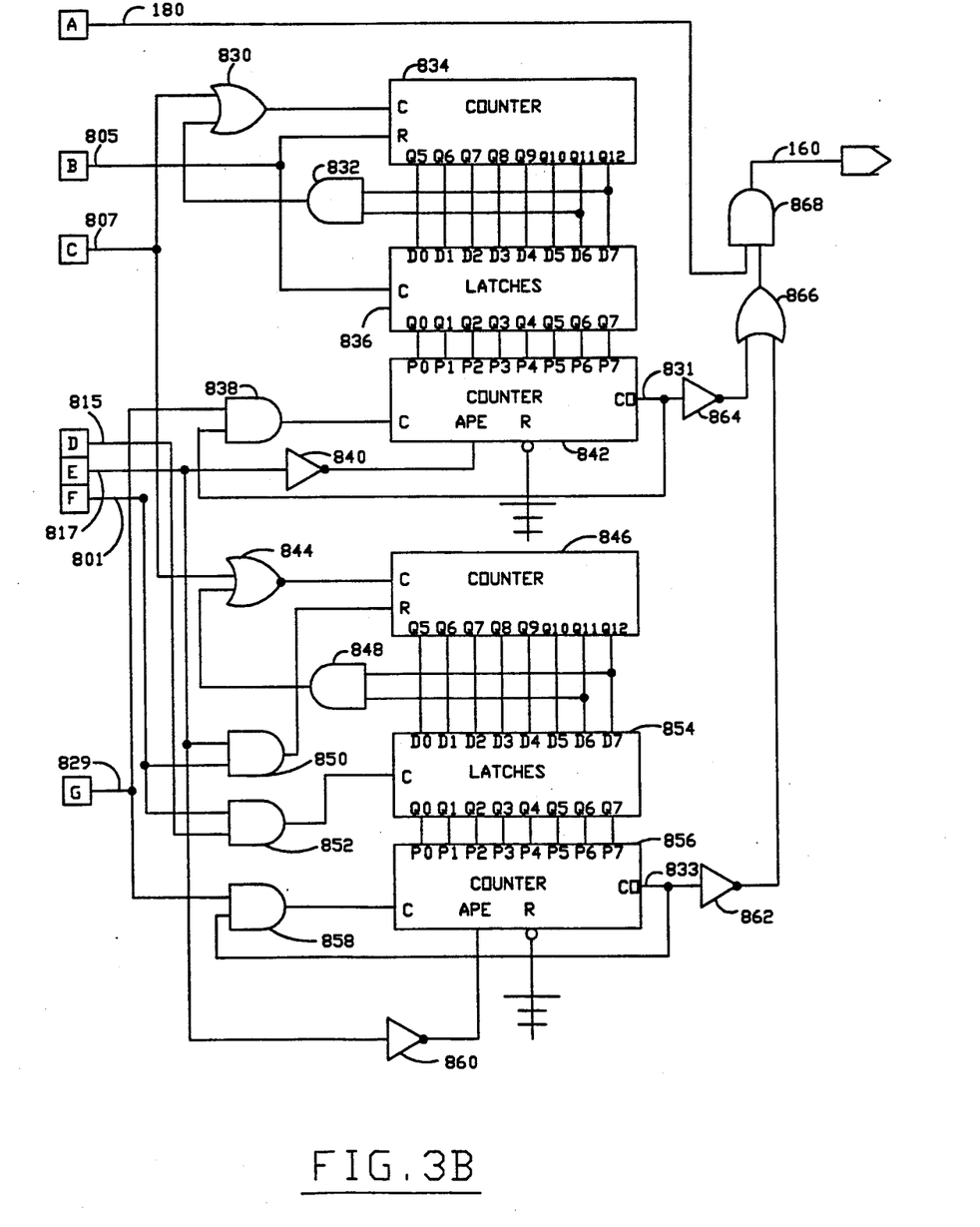

FIG. 3A and FIG. 3B together illustrate a schematic of VARP circuitry 20, as illustrated in FIG. 1. The schematic as illustrated provides a variable refractory period initiated on reset of the activity interval timing, as indicated by signals on line 150, and calculates a variable refractory period equal to 75 percent of the lesser of the average A-A and V-V intervals. Operation of the circuitry is as follows.

The 32 kHz crystal clock signal 170 is applied to clock counter 822 which divides the 32 kHz clock signal on line 70 down to a 2 kHz clock signal on line 825, a 1 kHz signal on line 821, and a 512 Hz signal on line 823. These clock signals are used to control all counters and timers in the VARP circuitry. The 512 Hz clock signal on line 823 is applied to ring counter 828 to provide an approximately 170 Hz clock signal on line 829.

Counter 816 is a ring counter, acting as a sequencer. Counter 816 is reset by positive-going signals on line 150, indicative of reset of the activity interval timer. Counter 816 defines three functional intervals following reset, indicated by sequential high signals on lines 817 and 819. When the Q3 output of counter 816 goes high, this acts to disable the counter from further counting until subsequent reset. The 2 kHz signal on line 825 serves as a clock signal for counter 816. Signals on line 150 are inverted by inverter 820 and also serve to clock ring counter 824. As discussed above, the VARP circuit updates the averaged V-V interval measurement every 4 beats. Counter 824 generates a high signal on line 801 every 4th beat. This signal is used to initiate calculation of a new V-V interval average. When line 819 goes high shortly thereafter, a reset signal is applied to counter 824 by means of AND gate 818, resetting the counter 824 until the next subsequent signal on line 150, which resets counter 816 and removes the reset signal from counter 824. Because the signal on line 150 is inverted by inverter 820, the trailing edge of the signal will be effective to clock counter 824 following removal of the reset signal provided by AND gate 818.

Counter 800 serves as a nonretriggerable 1-shot, reset by signals on line 180 via AND gate 804. Counter 800 is clocked via the 1 kHz clock signal on line 821, delivered through AND gate 802. After reset of counter 800, subsequent signals on line 180 are ineffective to reset this counter, until Q9 of the counter goes high, 250 ms thereafter. When Q9 of counter 800 goes high, the clock signal to the counter is disabled via inverter 806 and AND gate 802. With each reset of the counter, a high signal is generated on line 803 which serves to clock ring counter 808. Ring counter 808 corresponds to ring counter 824, and provides a high signal on line 805 with every 4th count, resetting itself via resistor 81?. The signal on line 805 is used by the circuitry for calculating the average A-A intervals to trigger an update of the A-A interval average.

Counter 812 serves as a 10 ms one-shot triggered by the 512 Hz signal on line 23, and providing a corresponding 10 ms pulse with each clock set. This signal is also used in determining the average A-A, average V-V, and variable refractory period intervals.

FIG. 3B illustrates the circuitry that calculates and implements the variable refractory intervals. Counter 834 is clocked by the 512 Hz signal on line 807, and reset by the on line 805. Counter 834 is disabled from further counting at overflow by means of AND gate 832, which prevents passage of the clock signal 807 through OR gate 830. The signal on line 805 indicative of the 4th counted atrial contraction on line 180 also serves to latch the Q outputs of counter 834 into latches 836, where they are then available to counter 842.

Counter 842 is a jam-in down-counter, loaded after each activity interval reset signal on line 150 via the Q2 output of counter 816 on line 817. On counter 842 reaching a count of zero, a high signal is generated on the carry out line 831 from counter 842, which disables further counting via AND gate 838.

Because the outputs of the 5th through 12th stages of counter 834 are applied to the 1st through 7th stages of counter 842, the number stored in counter 842 is approximately 1/16 of the value stored in counter 834, which in turn reflects the time required for 4 successive atrial sense events to occur. Because the clock frequency applied to counter 842 is 1/3 the clock frequency applied to counter 834, the net result is that counter 842 defines a time interval from loading to zero count equal to 75 percent of the average A-A interval. Because counter 842 is loaded on each reset of the activity timer, indicated by signals on line 150, it defines an atrial refractory period beginning with activity timer reset, extending thereafter for 75 percent of the average A-A interval.

Counter 846, latches 854 and counter 856 define the refractory interval associated with the average V-V intervals. Functionally they operate equivalently to counters 834, 836 and 842, with some minor variations. Counter 846 is clocked by the 512 Hz clock signal on line 507, with counting disabled by overflow of the counter as indicated AND gate 842 which disables pass-through of the clock signal through OR gate 844. Counter 846 is reset in response to a count of 4 activity resets as indicated by a high signal on line 801, concurrent with a high signal on line 817, from the Q2 output of the sequencer counter 816. The outputs of the 5th through 12th stages of counter 846 are entered in latches 854 in response to detection of the 4th activity counter reset, indicated by a high signal on line 801, concurrent with line 815 from counter 816. Counter 856 is loaded with the number stored in latches 854 following each activity timer reset signal as indicated by a high signal on line 817, and counts down to zero, as indicated by a high carry out signal on line 833, which in turn disables further clocking of the counter via AND gate 858. In a fashion similar to that discussed above in conjunction with the atrial refractory period circuitry, counter 856 defines a period beginning with activity timer reset and extending for 75 percent of the average V-V interval.

The signals on lines 831 and 833, inverted by inverters 864 and 862, respectively, are applied OR gate 866 on the first of the two carry out lines 831 and 833 going high. This enables signals indicative of atrial contractions on line 180 to pass through AND gate 868 to line 160, where they are provided to the digital controller 10. Thus, expiration of the lesser of the two calculated variable refractory periods is effective to allow passage of subsequent atrial contractions.

The circuitry illustrated in FIGS. 3A and 3B can also be employed to calculate a refractory period following ventricular events, assuming that signals applied to the circuitry on line 150 occur with each ventricular pacing pulse and with each sensed ventricular contraction. However, in this case it would be necessary to alter the clock frequency used to clock counters 842 and 856 to provide for a lesser proportion of the calculated V-V and A-A intervals as a refractory period. For example, if a 60 percent value is desired as discussed previously in the application, the clock signals applied to counters 842 and 856 would have to be altered to approximately 200 Hz, up from approximately 170 Hz. This could be accomplished by substituting the kHz clock signal on line 821 as an input to ring counter 828 and applying the signal from Q5 counter output of to line 829. Alternatively, it would be possible to vary the calculated percentage of the average A-A and V-V intervals by varying the frequency of the clock signal supplied to counters 834 and 846. Variable control of the duration of the variable refractory period as a percentage of the average A-A and V-V intervals could be accomplished by providing a variable frequency clock generator to control operation of either counters 834 and 846 or of counters 842 and 856. For example, a voltage controlled oscillator might be employed, or a programmable digital timer, under control of the digital controller 10. While these embodiments are not specifically illustrated, they are believed to be within the scope of the present invention.

Similarly, while the invention as illustrated in the present application is embodied in the form of an add-on circuit which might be applicable to previous DDD pacemakers with atrial output disabled or for previous VDD pacemakers, it is also believed within the scope of the invention to provide the required variable refractory periods by means of a microprocessor-based pacemaker, in which calculations of the variable atrial refractory periods are performed by an arithmetic logic unit under software control. As such, the illustrated embodiment should be considered merely exemplary, and not limiting with regard to the following claims.

In conjunction with the above specification, we claim:

1. A cardiac pacemaker, comprising:
   atrial sensing means for sensing contractions of the atrium;
   ventricular sensing means for sensing contractions of the ventricle;
   ventricular pulse generating means for generating ventricular pacing pulses;
   a-V interval determining means for determining an A-V interval initiated in response to sensing of an atrial contraction by said atrial sensing means and for triggering generation of a ventricular pacing pulse by said ventricular pulse generating means on the expiration of said A-V interval;
   V-V interval determining means for determining a V-V interval following generation of a ventricular pacing pulse by said ventricular pulse generating means and following sensing of a ventricular contraction by said ventricular sensing means, said V-V interval determining means also triggering said ventricular pulse generating means to generate a ventricular pacing pulse at the expiration of said V-V interval;
   sensor means for sensing physiologic demand for cardiac output and for varying the duration of said V-V interval and correspondence with said sensed demand for cardiac output; and
   refractory interval determining means for determining a variable refractory period for preventing a natural atrial contraction occurring therein from causing said pacemaker to initiate timing of said A-V interval, said refractory interval determining means comprising A-A interval measurement means for measuring the intervals separating proceeding atrial contractions and A-A interval averaging means for processing said measured A-A intervals to determine an average A-A interval and ventricular interval measuring means for measuring the intervals separately preceding previous ventricular contractions and V-V interval averaging means for processing said measured V-V intervals for determining an average V-V intervals, said refractory interval determining means defining said variable refractory as a function of both said average A-A and V-V intervals.

2. A pacemaker according to claim 1 wherein said refractory interval defining means defines said variable refractory period as a function of the lesser of said average interval separating preceding atrial contractions and said average interval separating preceding ventricular contractions.

3. A pacemaker according to claim 2 wherein said variable refractory period is a specified percentage of the lesser of said average interval separating preceding atrial contractions and said average interval separating preceding ventricular contractions.

4. A pacemaker according to claim 1 or claim 2 or claim 3 wherein said variable refractory period is initiated in response to generation of a ventricular pacing pulse by said ventricular pulse generator means.

5. A pacemaker according to claim 4 wherein said variable refractory period is approximately 60% of the lesser of said average interval separating preceding atrial contractions and said average interval separating preceding ventricular contractions.

6. A pacemaker according to claim 1 wherein said V-V interval determining means defines a first, variable interval following generation of a ventricular pacing pulse by said ventricular pulse generator means, the duration of said variable interval determined by the physiologic demand for cardiac output as measured by said sensor means, said V-V determining means further defining a fixed interval following said variable interval, at the expiration of which said V-V interval defining means triggers generation of a ventricular pacing pulse by said ventricular pulse generator means.

7. A pacemaker according to claim 6 wherein said variable refractory period determined by said refractory interval determining means is initiated in response to expiration of said variable interval determined by said V-V interval determining means.

8. A pacemaker according to claim 7 wherein said variable refractory period is approximately 75% of the lesser of said average interval separating preceding atrial contractions and said average intervals separating preceding ventricular contractions.

9. A pacemaker according to claim 1 or claim 2 wherein said variable refractory period is initiated in response to sensing of an atrial contraction by said atrial sensing means.

10. A pacemaker according to claim 9 wherein said variable refractory period is approximately 75% of the lesser of said average intervals separating proceeding atrial contractions and said average intervals separating proceeding ventricular contractions.

* * * * *